(12) United States Patent
Wight

(10) Patent No.: US 10,549,056 B2
(45) Date of Patent: Feb. 4, 2020

(54) AIRWAY MANAGEMENT DEVICE AND METHOD OF MANUFACTURE

(71) Applicant: Ronald Craig Wight, Singapore (SG)

(72) Inventor: Ronald Craig Wight, Singapore (SG)

( * ) Notice: Subject to any disclaimer, the term of this patent is extended or adjusted under 35 U.S.C. 154(b) by 667 days.

(21) Appl. No.: 15/117,267

(22) PCT Filed: Feb. 9, 2015

(86) PCT No.: PCT/SG2015/000035
§ 371 (c)(1),
(2) Date: Aug. 8, 2016

(87) PCT Pub. No.: WO2015/119577
PCT Pub. Date: Aug. 13, 2015

(65) Prior Publication Data
US 2016/0346493 A1    Dec. 1, 2016

(30) Foreign Application Priority Data
Feb. 10, 2014 (SG) ................ 2014011720

(51) Int. Cl.
*A61M 16/04* (2006.01)
(52) U.S. Cl.
CPC .... *A61M 16/0486* (2014.02); *A61M 16/0409* (2014.02); *A61M 16/0415* (2014.02); *A61M 16/0445* (2014.02); *A61M 16/0463* (2013.01); *A61M 16/0431* (2014.02); *A61M 16/0434* (2013.01); *A61M 2202/0208* (2013.01); *A61M 2205/0216* (2013.01); *A61M 2207/00* (2013.01)

(58) Field of Classification Search
CPC .............. A61M 16/04; A61M 16/0409; A61M 16/0415; A61M 16/0431; A61M 16/0434; A61M 16/0445; A61M 16/0463; A61M 16/0486; A61M 16/0488; A61M 2205/0216; A61M 2207/00
See application file for complete search history.

(56) References Cited

U.S. PATENT DOCUMENTS

| | | |
|---|---|---|
| 4,509,514 A | 4/1985 | Brain |
| 4,995,388 A | 2/1991 | Brain |
| 5,241,956 A | 9/1993 | Brain |
| 5,249,571 A | 10/1993 | Brain |
| 5,282,464 A | 2/1994 | Brain |
| 5,297,547 A | 3/1994 | Brain |
| 5,303,697 A | 4/1994 | Brain |
| 5,305,743 A | 4/1994 | Brain |

(Continued)

FOREIGN PATENT DOCUMENTS

| | | |
|---|---|---|
| CN | 202005940 U | 10/2011 |
| CN | 103203058 A | 4/2013 |

(Continued)

*Primary Examiner* — Joseph D. Boecker
(74) *Attorney, Agent, or Firm* — King & Schickli, PLLC

(57) ABSTRACT

An airway management device comprising a body having a proximal end for receiving an oxygen supply tube and an distal end for insertion into a trachea of a patient; said body including a linear portion adjacent to the proximal end and a curved portion adjacent to the distal end; said body including an external shell and having a first bore through said shell for receiving the oxygen supply tube; wherein flexural strength for said airway management device is provided by said shell.

26 Claims, 16 Drawing Sheets

(56) References Cited

U.S. PATENT DOCUMENTS

| | | |
|---|---|---|
| 5,355,879 A | 10/1994 | Brain |
| 5,391,248 A | 2/1995 | Brain |
| 5,513,627 A * | 5/1996 | Flam ................ A61M 16/0463 |
| | | 128/200.26 |
| 5,584,290 A | 12/1996 | Brain |
| 5,632,271 A | 5/1997 | Brain |
| 5,682,880 A * | 11/1997 | Brain ................ A61M 16/0488 |
| | | 128/200.26 |
| 5,711,293 A | 1/1998 | Brain |
| 5,896,858 A | 4/1999 | Brain |
| 6,079,409 A | 6/2000 | Brain |
| 6,439,232 B1 | 8/2002 | Brain |
| 6,631,720 B1 | 10/2003 | Brain |
| 6,705,318 B1 | 3/2004 | Brain |
| 6,792,948 B2 | 9/2004 | Brain |
| 6,918,388 B2 | 7/2005 | Brain |
| 7,004,169 B2 | 2/2006 | Brain |
| 7,097,802 B2 | 8/2006 | Brain |
| 7,128,071 B2 | 10/2006 | Brain |
| 7,134,431 B2 | 11/2006 | Brain |
| 7,156,100 B1 | 1/2007 | Brain |
| 7,159,589 B2 | 1/2007 | Brain |
| RE39,508 E | 4/2007 | Parker |
| RE39,938 E | 12/2007 | Brain |
| 7,305,985 B2 | 12/2007 | Brain |
| 7,493,901 B2 | 2/2009 | Brain |
| 7,506,648 B2 | 3/2009 | Brain |
| 7,694,682 B2 | 4/2010 | Petersen et al. |
| 7,780,900 B2 | 8/2010 | Cook |
| 7,784,464 B2 | 8/2010 | Cook |
| 7,806,119 B2 | 10/2010 | Nasir |
| 7,896,007 B2 | 3/2011 | Brain |
| 7,900,632 B2 | 3/2011 | Cook |
| 7,934,502 B2 | 5/2011 | Cook |
| 8,215,307 B2 | 7/2012 | Nasir |
| 8,449,713 B2 | 5/2013 | Brain |
| 8,485,188 B2 | 7/2013 | Nasir |
| 8,590,535 B2 | 11/2013 | Dubach |
| 8,622,060 B2 | 1/2014 | Cook |
| 8,631,796 B2 | 1/2014 | Cook |
| 8,776,797 B2 | 7/2014 | Brain |
| 8,778,248 B2 | 7/2014 | Nasir |
| 8,783,256 B2 | 7/2014 | Brain |
| 8,887,716 B2 | 11/2014 | Dubach |
| 8,978,657 B2 | 3/2015 | Sandmore et al. |
| 8,978,658 B2 | 3/2015 | Cook |
| 9,027,559 B2 | 5/2015 | Brain |
| 9,265,904 B2 | 2/2016 | Esnouf |
| 9,265,905 B2 | 2/2016 | Nasir |
| 9,266,268 B2 | 2/2016 | Nasir |
| 9,271,631 B2 | 3/2016 | Leeflang et al. |
| 9,320,864 B2 | 4/2016 | Cook |
| 9,463,296 B2 | 10/2016 | Stix |
| 9,475,223 B2 | 10/2016 | Nasir |
| 9,480,806 B2 | 11/2016 | Brain |
| 9,498,591 B2 | 11/2016 | Brain |
| 9,522,245 B2 | 12/2016 | Brain |
| 9,662,465 B2 | 5/2017 | Brain |
| 9,675,772 B2 | 6/2017 | Brain |
| 9,694,150 B2 | 7/2017 | Brain |
| 2003/0037790 A1 * | 2/2003 | Brain ................ A61M 16/04 |
| | | 128/207.14 |
| 2003/0051734 A1 | 3/2003 | Brain |
| 2003/0060764 A1 | 3/2003 | Dua et al. |
| 2003/0131845 A1 | 7/2003 | Lin |
| 2004/0089307 A1 | 5/2004 | Brain |
| 2004/0129272 A1 * | 7/2004 | Ganesh ................ A61M 16/04 |
| | | 128/207.14 |
| 2005/0103345 A1 | 5/2005 | Brain |
| 2005/0133037 A1 | 6/2005 | Russell |
| 2007/0102001 A1 | 5/2007 | Brain |
| 2008/0053455 A1 | 3/2008 | Brain |
| 2008/0060655 A1 | 3/2008 | Brain |
| 2008/0092903 A1 | 4/2008 | Nash |
| 2008/0099026 A1 * | 5/2008 | Chang ................ A61M 16/0463 |
| | | 128/207.15 |
| 2008/0115783 A1 | 5/2008 | Brain |
| 2008/0142017 A1 | 6/2008 | Brain |
| 2008/0308109 A1 | 12/2008 | Brain |
| 2009/0007920 A1 | 1/2009 | Brain |
| 2009/0090356 A1 | 4/2009 | Cook |
| 2009/0133701 A1 | 5/2009 | Brain |
| 2009/0145438 A1 | 6/2009 | Brain |
| 2010/0147309 A1 | 6/2010 | Cuevas et al. |
| 2010/0313893 A1 | 12/2010 | Brain |
| 2011/0203594 A1 | 8/2011 | Brain |
| 2011/0220117 A1 * | 9/2011 | Dubach ................ A61M 16/04 |
| | | 128/207.14 |
| 2011/0226256 A1 | 9/2011 | Dubach |
| 2011/0290246 A1 | 12/2011 | Zachar |
| 2012/0010467 A1 | 1/2012 | Brain |
| 2012/0048279 A1 | 3/2012 | Brain |
| 2012/0090609 A1 * | 4/2012 | Dubach ................ A61M 16/04 |
| | | 128/204.18 |
| 2012/0145160 A1 | 6/2012 | Brain et al. |
| 2012/0174920 A1 | 7/2012 | Barkai et al. |
| 2012/0211010 A1 | 8/2012 | Brain et al. |
| 2012/0283513 A1 | 11/2012 | Leeflang et al. |
| 2013/0125897 A1 | 5/2013 | Baska |
| 2013/0239959 A1 | 9/2013 | Brain |
| 2013/0247907 A1 | 9/2013 | Brain |
| 2013/0247917 A1 | 9/2013 | Brain |
| 2013/0269689 A1 * | 10/2013 | Brain ................ A61M 16/04 |
| | | 128/200.26 |
| 2013/0324798 A1 * | 12/2013 | Molnar ................ A61M 16/04 |
| | | 600/120 |
| 2014/0000624 A1 | 1/2014 | Miller |
| 2014/0323806 A1 | 10/2014 | Brain |
| 2015/0083138 A1 | 3/2015 | Brain |
| 2015/0114400 A1 | 4/2015 | Dubach |
| 2015/0246196 A1 | 9/2015 | Hansen et al. |
| 2015/0290413 A1 | 10/2015 | Dubach |
| 2016/0008562 A1 | 1/2016 | Sagales Manas et al. |
| 2016/0101254 A1 | 4/2016 | Hansen et al. |
| 2016/0114117 A1 | 4/2016 | Cook |
| 2016/0136373 A1 | 5/2016 | Hansen et al. |
| 2016/0184542 A1 | 6/2016 | Esnouf |
| 2016/0206841 A1 | 7/2016 | Vadivelu |
| 2016/0317768 A1 | 11/2016 | Nasir et al. |
| 2017/0209660 A1 | 7/2017 | Cook |

FOREIGN PATENT DOCUMENTS

| | | |
|---|---|---|
| JP | 2008-541817 A | 11/2008 |
| WO | 2012017213 A1 | 2/2012 |
| WO | WO2014166136 A1 | 10/2014 |

* cited by examiner

Figure 3
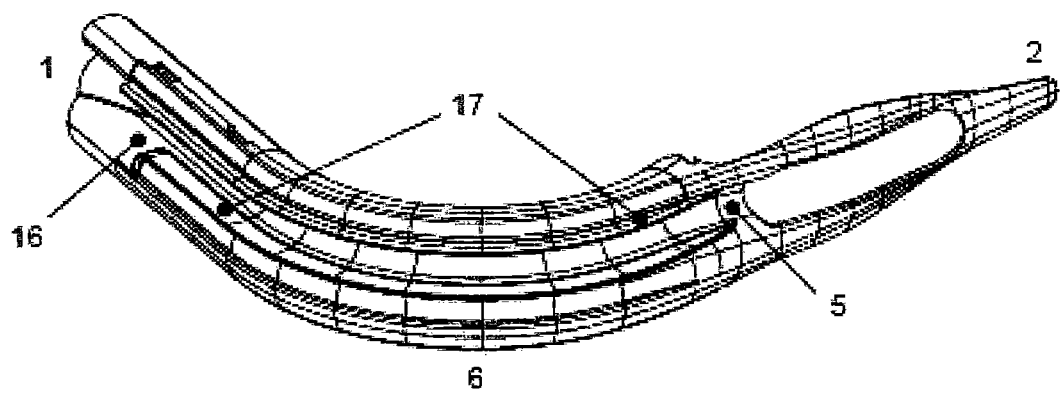
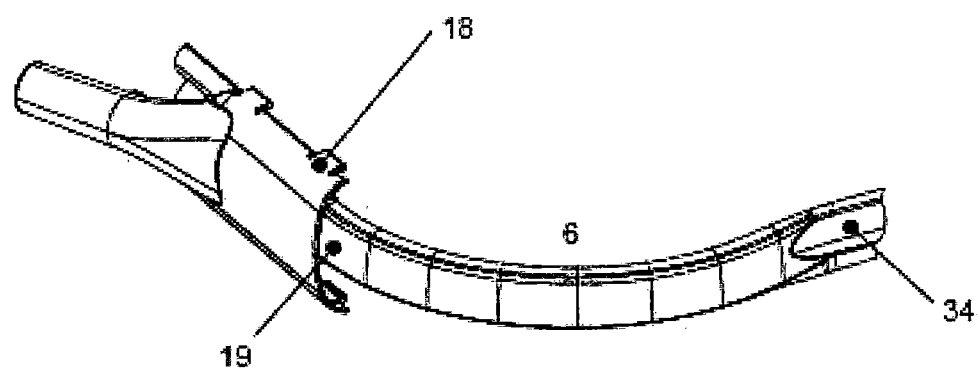
Figure 4

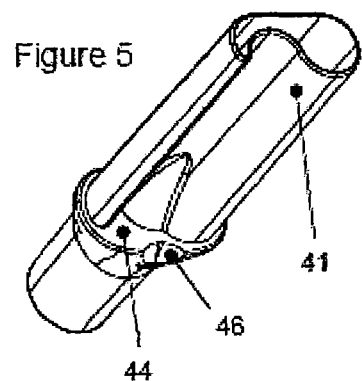
Figure 5
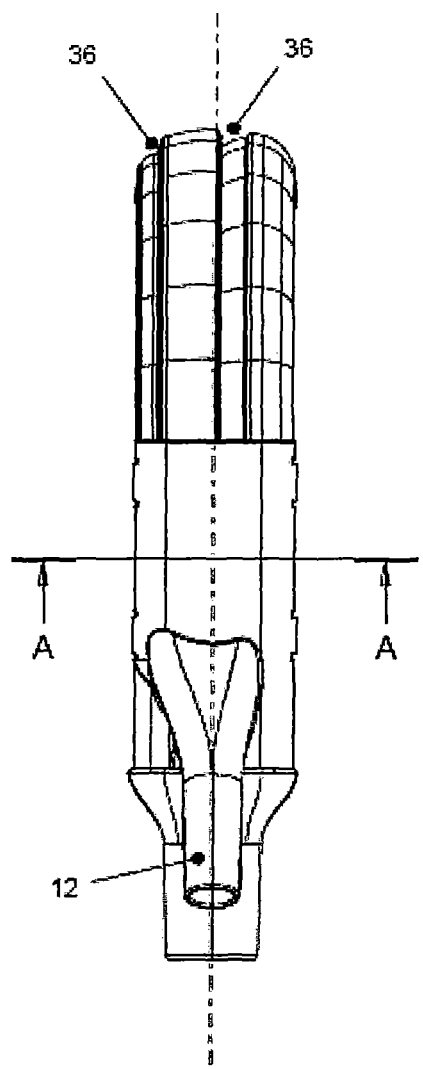
Figure 7
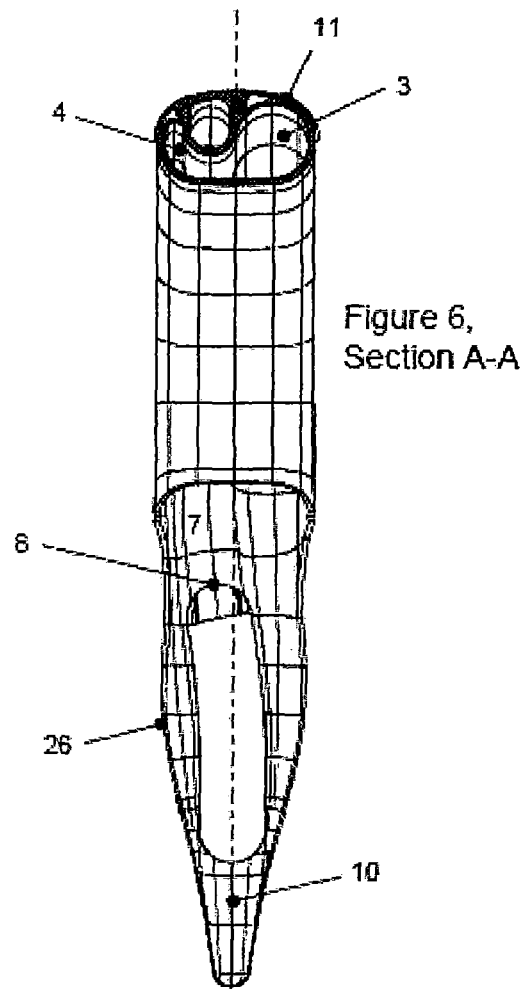
Figure 6, Section A-A

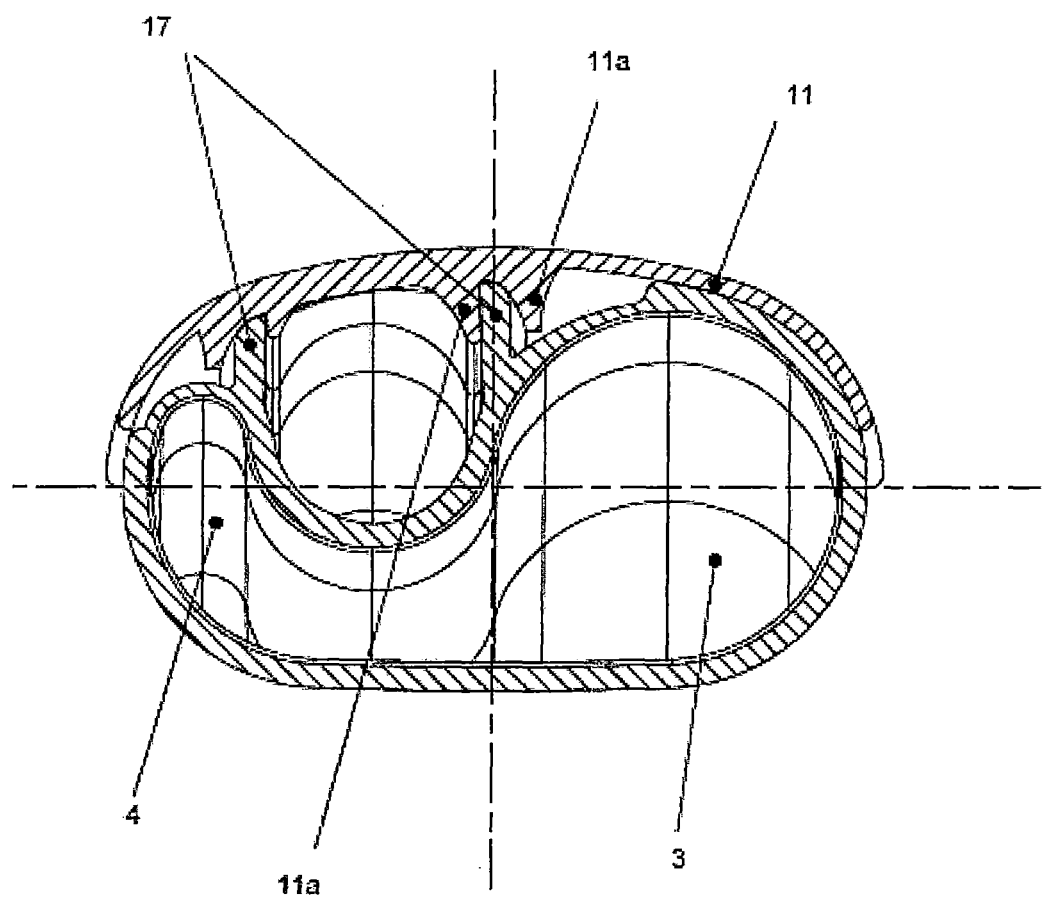
Figure 6a,
Section A-A x5

Section C-C

Section B-B

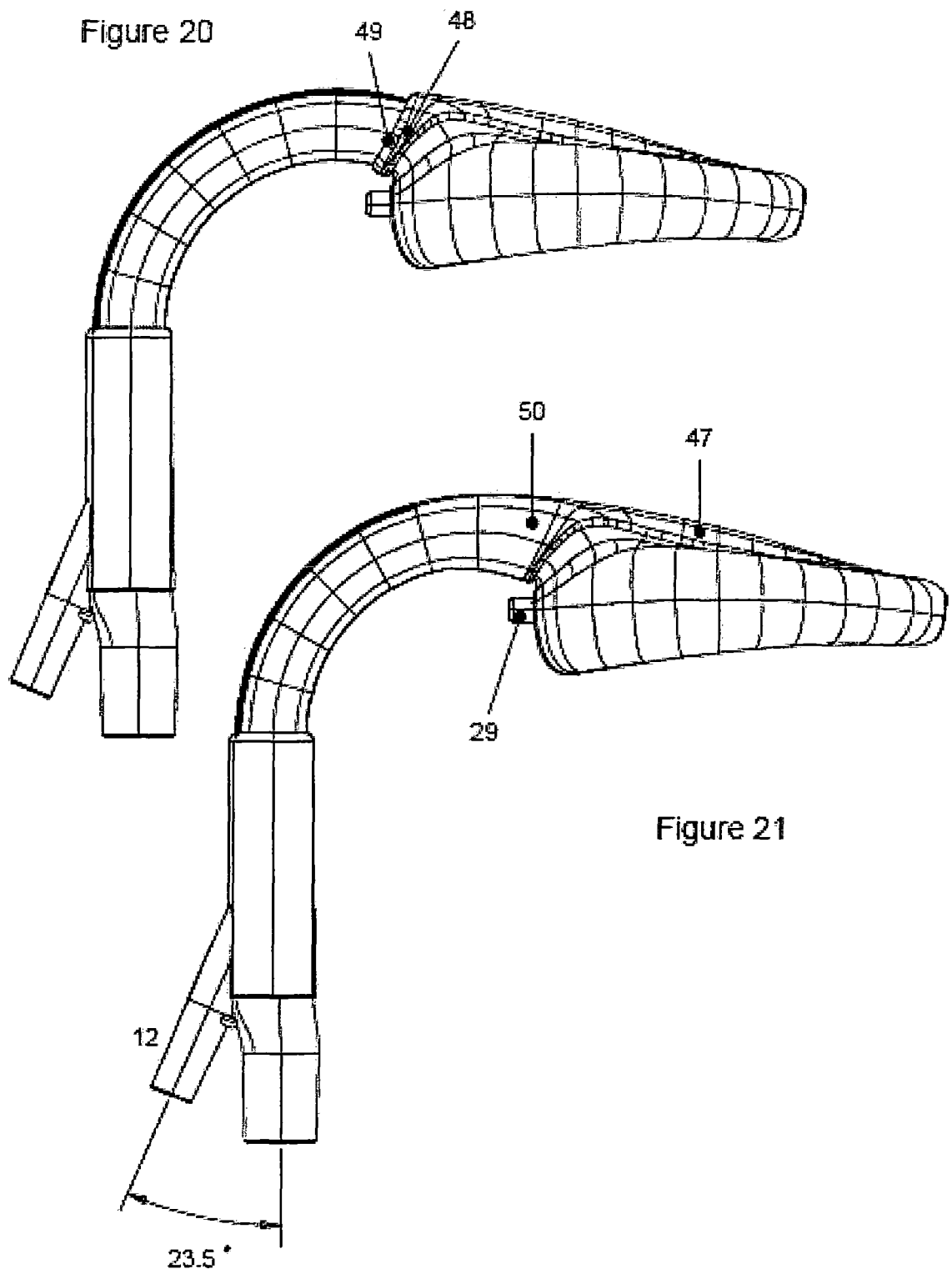

Figure 22
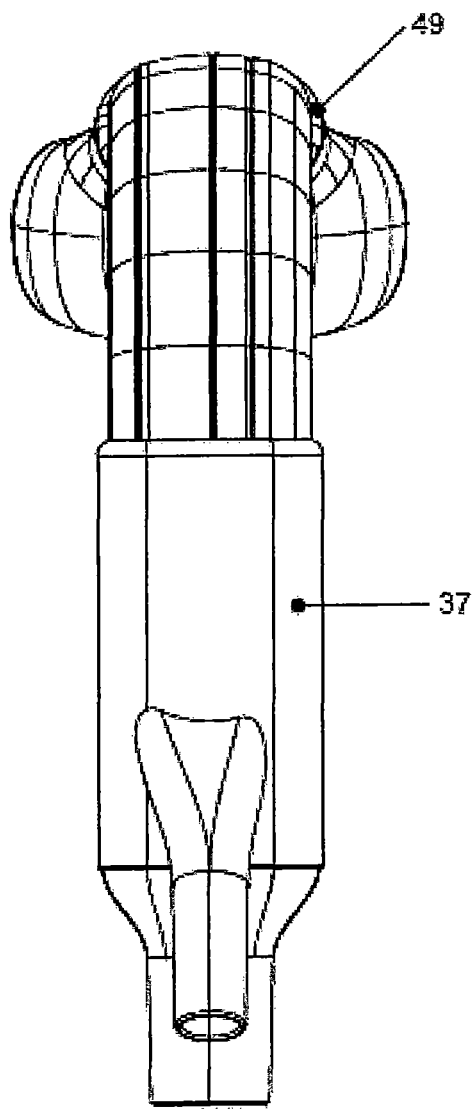
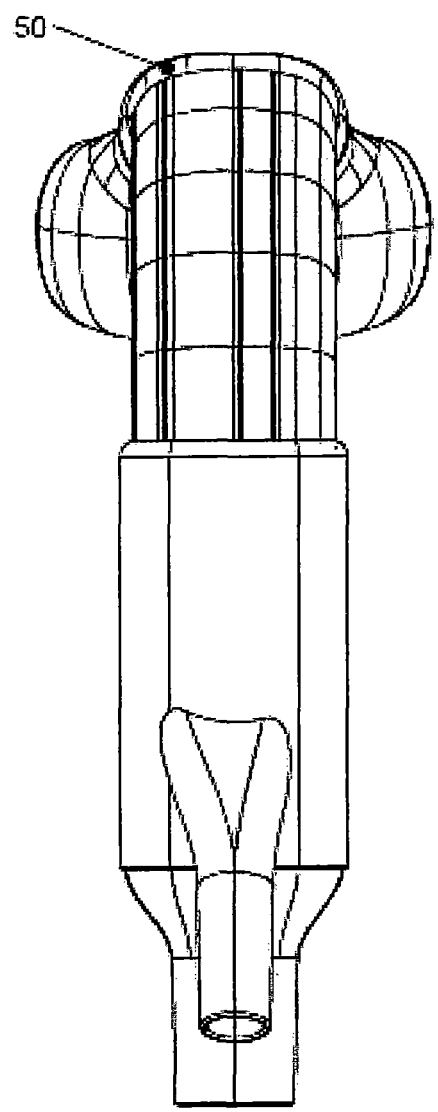
Figure 23

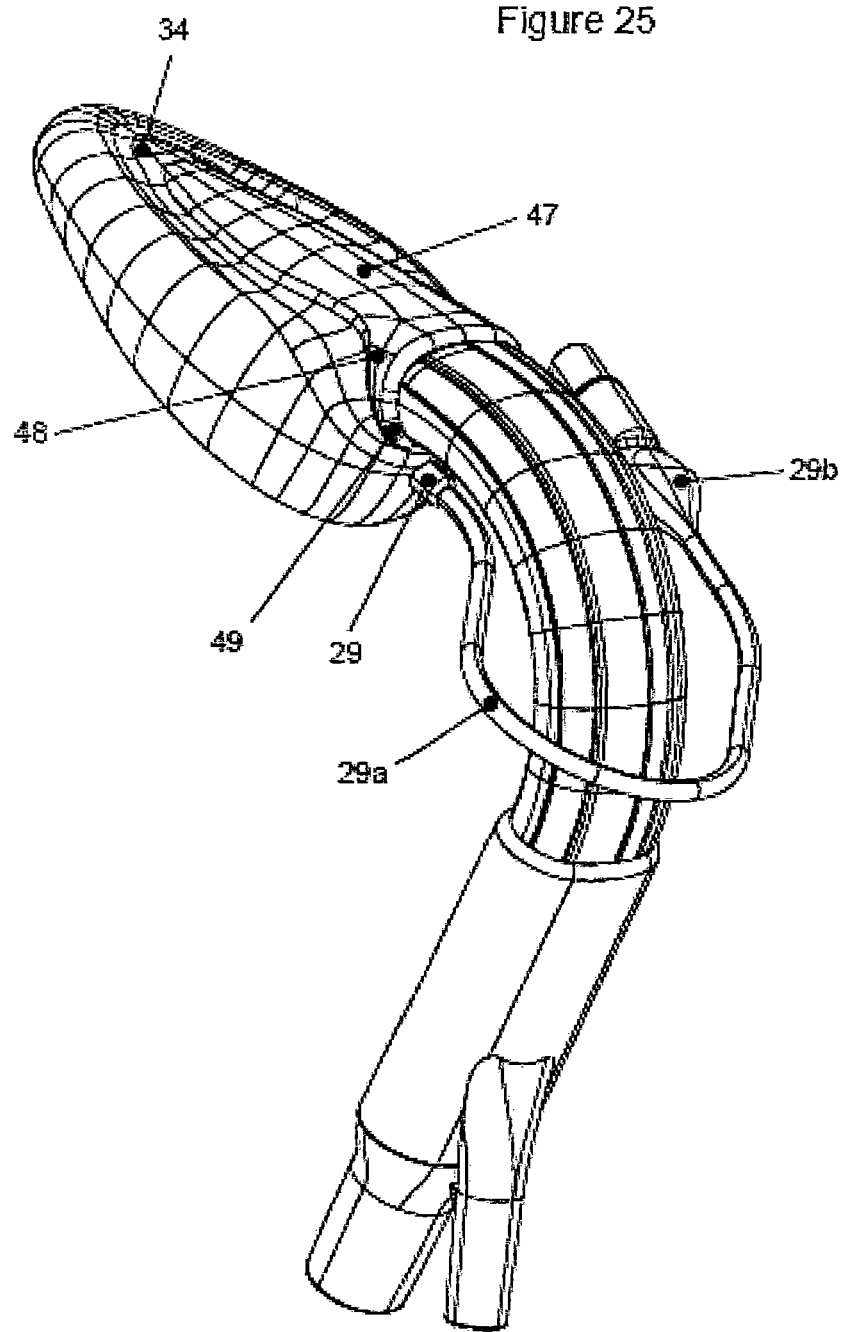

AIRWAY MANAGEMENT DEVICE AND METHOD OF MANUFACTURE

FIELD OF THE INVENTION

The invention relates to laryngeal devices, particularly those used for intubation of patients.

BACKGROUND

Several existing devices are used for facilitating spontaneous breathing in anaesthetised patients; traditionally, the Endotracheal Tube (ETT) and more recently the Laryngeal Mask Airway (LMA). The majority of these devices use an inflatable cuff(s) to create the anatomical seal and as a consequence there is an incidence of co-morbidity associated with their use; both physiological and anatomical. Subsequent refinement of the LMA has resulted in the development and introduction of supraglottic airway devices (SAD) with gastric drainage (GD). The reported advantages being ease of insertion, haemodynamic stability, decreased morbidity, improved respiratory mechanics and reduced incidence of pulmonary aspiration. An alternative development uses a pre-formed and non-inflatable cuff. Disadvantages of SAD with GD primarily relate to the configuration of the distal tip becoming bulbous by the presence of the gastric tube passing through the inflatable cuff and the associated structures employed; to present a flat profile of the distal tip when the inflatable cuff is deflated immediately prior to deployment and; prevent occlusion of the drain tube after the SAD is deployed and inflated in situ.

The visco-elastic characteristics of the materials used for construction of the various SAD's exert significant influence over the ability of the device to deliver the above stated advantages and contribute significantly to the disadvantages. SAD's use the same materials as existing LMA devices. Semi rigid PVC, vinyl elastomers and liquid silicone rubbers are predominant in combinations comprising a more rigid airway with a softer inflatable cuff whilst thermoplastic elastomers (TPE) are used for versions exhibiting a non-inflatable cuff. Those devices using PVC and LSR require the use of adhesives and solvents for bonding and joining the different components during manufacture. SAD's using TPE do not require adhesives as they are essentially a one piece more rigid airway tube covered with TPE material to form the required shape without an inflatable cuff.

SUMMARY OF INVENTION

In a first aspect the invention provides an airway management device comprising a body having a proximal end for receiving an oxygen supply tube and an distal end for insertion into a trachea of a patient; said body including a linear portion adjacent to the proximal end and a curved portion adjacent to the distal end; said body including an external shell and having a first bore through said shell for receiving the oxygen supply tube; wherein flexural strength for said airway management device is provided by said shell.

It will be appreciated that the first bore will include an adequate internal diameter to accommodate the oxygen supply tube in the form of an endotracheal tube;

In a second aspect the invention provides an airway management device comprising a body having a proximal end for receiving an oxygen supply tube and an distal end for insertion into a trachea of a patient; said body including a linear portion adjacent to the proximal end and a curved portion adjacent to the distal end, and a passage arranged to receive a gastric drain tube; a toroidal shaped membrane having a first and second opposed edged, said first edge moulded to a corresponding portion of the body and the second edge moulded to a corresponding second portion of the body, said first and second portions in spaced relation, the membrane forming an inflatable cuff.

Accordingly, the shell acts as an exoskeleton, protecting the oxygen supply and any other device placed therein during the insertion process. Further, by providing a first bore of sufficient size to receive the oxygen supply tube, the body will include a moment of inertia for the cross-sectional shape to provide a high degree of stiffness. The cross-sectional shape and selection of material may therefore allow considerable scope for selecting the required flexural stiffness for the airway management device. In the current embodiment, the body may simply be referred to as an airway tube.

The first bore may be a non-symmetrical shape having two lobes, having two portions arranged to receive and position the oxygen supply tube in one lobe, or a first passage, and an endoscope in the other lobe or second passage. By shaping the first bore, and in particular, the lobes the oxygen supply tube and endoscope may be confined to the particular lobe and so separate from each other, despite being positioned within an open first bore.

The body may include a second bore for containing a gastric drain tube. In the case of having the first and second passages as mentioned above, the second bore may then be considered a third passage.

The device according to the present invention may use methods of manufacturing that do not require adhesives. Rather, in one embodiment, it may utilise the self-adhesive properties of softer and more elastic TPE to the more rigid polypropylene substrate. In terms of visco-elasticity, a polyolefin material such as polypropylene may be used for the more rigid airway and TPE compound (using the same polypropylene as the base material) may be used for the inflatable cuff which offers superior elastic response and reduced hysteresis. By virtue of doing so, it allows for the introduction of numerous and desirable features for a SAD with GD.

Furthermore, the invention describes a SAD with GD that in addition to maintaining an airway as described, it also provides for blind intubation simultaneous with gastric access and the ability to visually evaluate in situ via endoscopy. Prior art describes LMA and SAD that do not offer such diverse functionality.

A possible application of the device according to the present invention may include where the patient is to be transferred to an intensive care facility. In such instances the LMA may be removed and replaced with an endotracheal tube.

An advantage of this invention may include that the device itself, by virtue of the airway tube structure, guides the ET Tube into position quickly and effectively with minimal trauma and loss of oxygen supply if intubation becomes a necessary requirement toward protecting the wellbeing of the patient. Positioning of the ET Tube may then be confirmed via endoscopy. The device described by the invention may then be removed whilst the ET Tube remains in situ.

BRIEF DESCRIPTION OF DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

FIG. 3 is an isometric view of the body of FIG. 1;

FIG. 4 is an isometric view of the insert of FIG. 2;

FIG. 5 is an isometric view of an oxygen supply adaptor of an airway management device according to one embodiment of the present invention;

FIG. 6 is a cross sectional view of the body of FIG. 7;

FIG. 6a is a detail cross sectional view of the body of FIG. 7;

FIG. 7 is an isometric view of the body of FIG. 1;

FIG. 20 is a side elevation view of the body of FIG. 18;

FIG. 21 is a side elevation view of the body of FIG. 19;

FIG. 22 is a back elevation view of the body of FIG. 18;

FIG. 23 is a back elevation view of the body of FIG. 19;

FIG. 25 is an isometric view of the body of FIG. 24.

DESCRIPTION OF INVENTION

Figure 1:
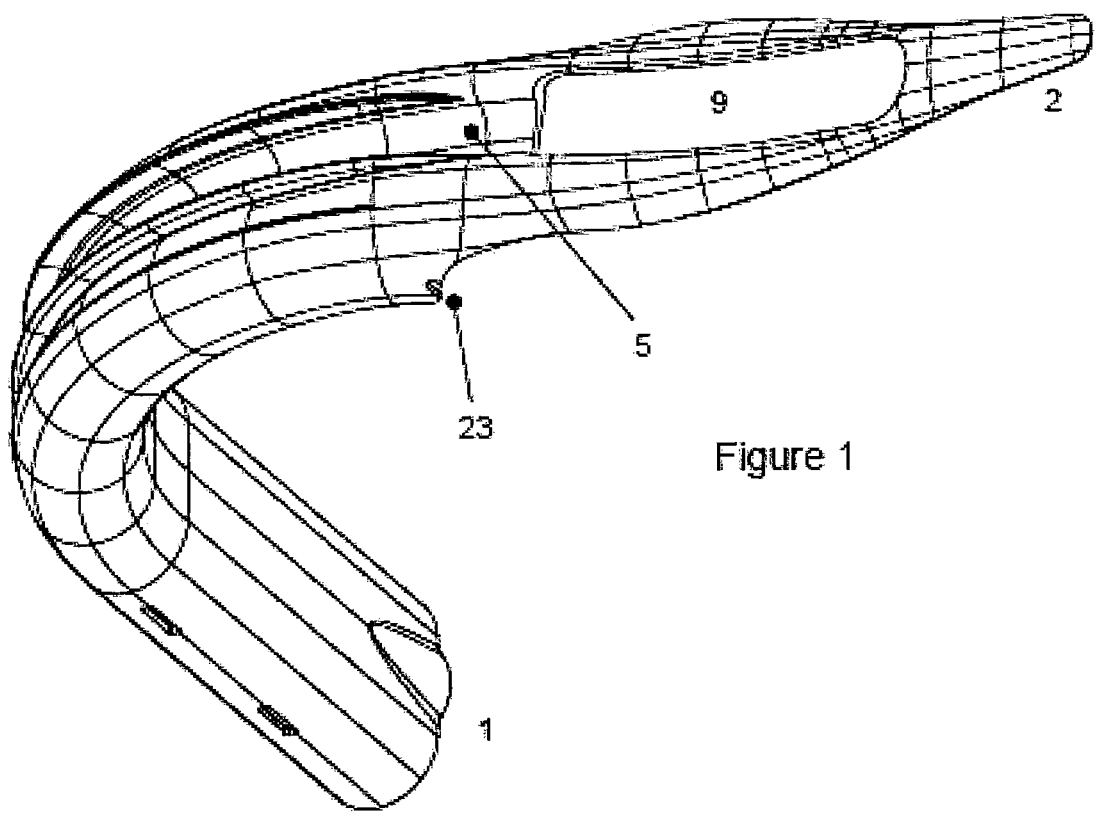
FIG. 1 is an isometric view of a body of an airway management device according to one embodiment of the present invention.

In the context of this description, the invention is henceforth described as if it were inserted in a supinely positioned patient. The airway management device includes a body, such as the airway tube (FIGS. 1 and 3) extending from the proximal end 1 of the device through to the distal tip 2. The horizontal cross section A-A (FIG. 6) through the straight portion of the proximal airway tube, shows the primary 3 and secondary passage 4 configured either side of the median plane. This configuration forms a shell providing a first moment of area greater than a similarly dimensioned circular or elliptical cross section. This provides the device with sufficient flexural strength and so acting as an exoskeleton as compared with prior art devices where much of the flexural strength is derived from components within the device, and so demonstrating an endo-skeleton structure.

Figure 17:
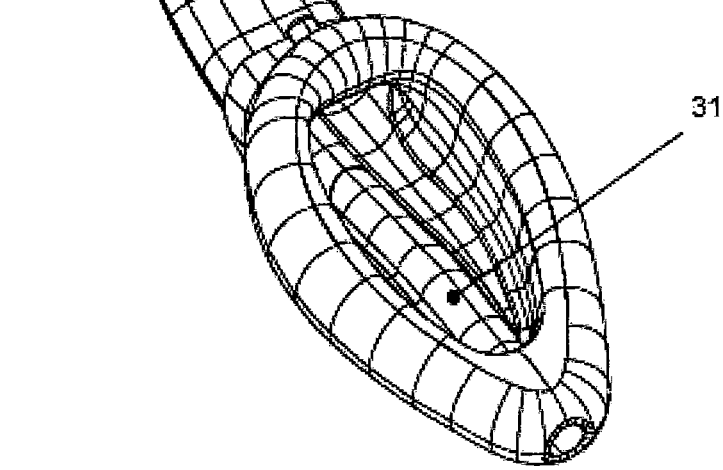
FIG. 17 is an isometric of a receiving tube of an airway management device according to a further embodiment of the present invention.

Inserted into the airway tube proximal opening is an adaptor (FIGS. 5 and 17), which facilitates connection to an oxygen supply as well as combining into a more rigid structure able to cope with and to facilitate the forces of circumduction during insertion. The parallel and sagittal planar relationship of these two passages defines an additional partial posterior channel 5 that; together with an intermediate strip (FIGS. 2 and 4), creates a laterally offset third passage to facilitate gastric drainage.

Figure 9:
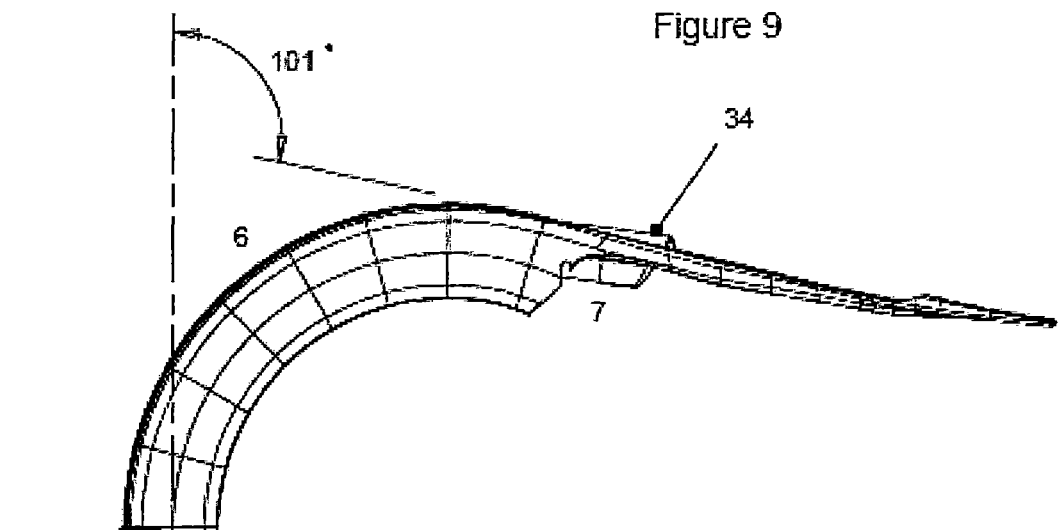
FIG. 9 is an elevation view of the body of FIG. 1.
Figure 10:
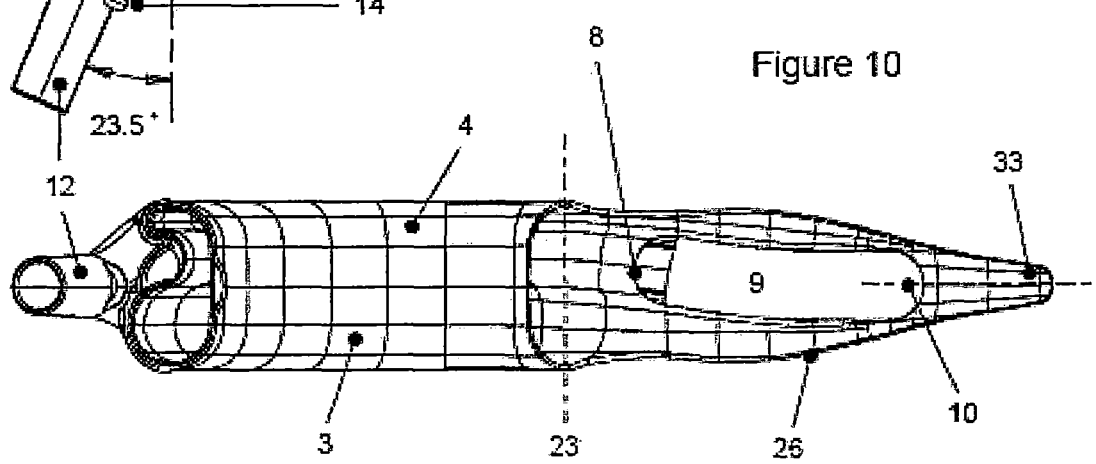
FIG. 10 is a plan view of the body of FIG. 1.

Cross section A-A (FIG. 6) progresses inferiorly through an anatomically approximated curvature 6 of approximately 101 degrees (FIG. 9), parallel to the median plane, whereupon it transitions from a closed cross section to an open cross section (FIGS. 8 and 9) coinciding with the ventral opening of the device 7, where the primary and secondary passages terminate openly. Within this opening, the primary passage provides gaseous communication. When the adaptor is removed, this primary passage 3 allows for blind intubation (FIG. 10). The secondary passage 4 provides for endoscopic access during blind intubation as well as a secondary passage for spontaneous breathing during blind intubation.

Continuing inferiorly from this transition, the airway tube cross section maintains the semi-circular contour of the partial posterior channel 5 until reaching the proximal end 8 of the medial slot 9, a feature congruent with the anterior or ventral opening. When viewed anteriorly toward the frontal plane (FIGS. 6 and 10), the medial slot provides a route of progressive curvature for gastric drainage, from the partial posterior channel 5 through the medial slot to the anterior side of the distal airway tube; aligning the route for gastric drainage to the median plane of the distal tip 10; allowing the passing of a gastric drainage or suction tube with minimal frictional resistance.

Attached to the posterior of the airway tube is the intermediate strip (FIGS. 2 and 4) which exhibits curvature 6 in the sagittal plane matching the airway tube and horizontal cross section 11 providing geometric conformance and attachment to the airway tube (FIGS. 6 and 6a). The proximal intermediate strip (FIGS. 9 and 10) is defined by a tubular feature 12 that serves as the entry point for gastric drainage or suction tube; and whose median axis when viewed laterally, adopts an angle of approximately 23.5 degrees with the horizontal plane coincident with the median axis 13 through the proximal end of the airway tube (FIGS. 9 and 21). When positioned on the airway tube, the intermediate strip covers the partial posterior channel 5 which is essentially an elongate recess which together defines a third passage as a route for gastric drainage. The intermediate strip, once positioned, is flush with an external surface of the body of the device. The distal end of the intermediate strip terminates at the proximal end of the aforementioned medial slot 8. Continuing inferiorly to the distal extremity 2, the airway tube cross section progressively reduces in width and first moment of area. Horizontal cross sections throughout this transition exhibit ventrally concave curvature i.e. maintaining the posterior contour 34 were the intermediate strip (FIGS. 2, 4 and 9) to continue until the distal extremity of the airway tube.

Figure 15:
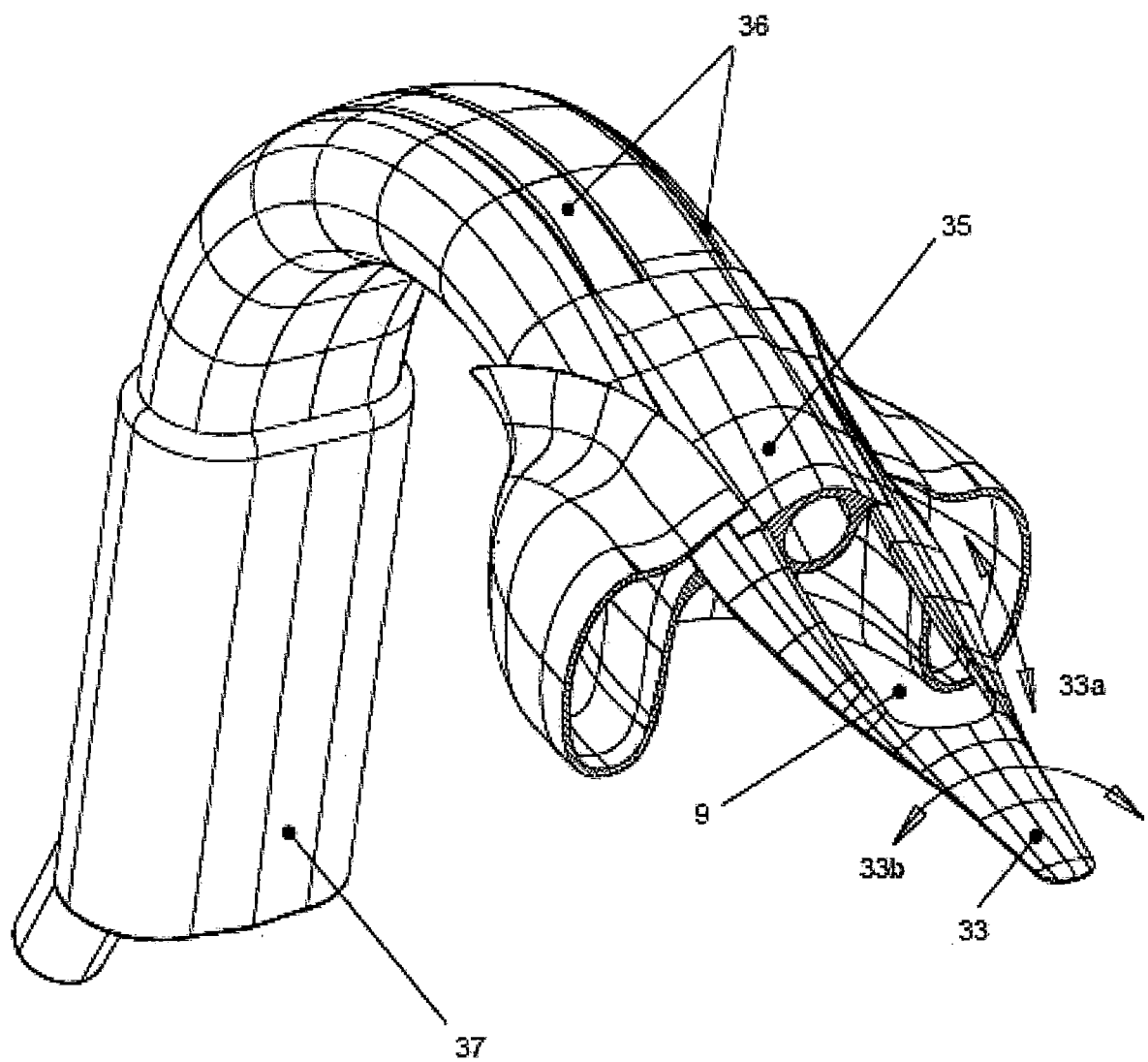
FIG. 15 is an isometric and cross sectional view of the body of FIG. 12.

When combined with the elastic properties of the polyolefin material, the ventrally concave curvature parallel to the medial slot 33a and horizontally through 33b the medial slot creates a compound curvature (FIG. 15) or partial conical spring (Belleville washer) that encourages an immediate elastic response from the polyolefin material during flexure; thus maintaining contact between posterior airway tube and the posterior hypo-pharynx during insertion, without excessive force contributing to co-morbidity and soft tissue damage.

In pure mechanical terms, the distal end of the airway tube can be considered as the fixed support, whilst the airway tube by itself can be considered to act as a cantilever beam. Force exerted through the straight proximal portion of the airway tube during insertion concentrates flexion and extension through a horizontal axis coincident with two laterally opposed slots 23. The primary passage being larger in diameter than the secondary passage allows a degree of rotation around the medial axis of the proximal airway tube that can be transferred as torsion through to the distal tip. SAD's using semi-rigid PVC materials for the airway tube behave in a viscous manner i.e. when force is applied they resist shear and exhibit linear strain (relationship between change in length to original length) for the duration of the applied force. However, these forces are dissipated into the PVC material such that when force is released, PVC will not immediately respond and return to its original state. This lost energy, or hysteresis, is a significant disadvantage of prior art based on PVC materials. Polyolefin materials such as polypropylene exhibit a superior visco-elastic response, characterised by elastic rather than viscous response.

During insertion, the forces transferred through the airway tube are manifested by circumduction. As a consequence, hysteresis in the materials used by existing prior may prevent the distal tip being correctly in situ with the upper oesophageal sphincter. Prior art describes the possibility of the distal tip entering the larynx or, the distal tip of the LMA or SAD may fold under, a phenomenon described as down-folding. Unlike other LMA or SAD, this invention uses an airway tube that extends from the proximal end to the distal tip and whose form and function utilise the more immediate visco-elastic response of a rigid polyolefin material. Where other SAD's describe a ventral displacement of the distal tip in relation to a dorsal or posterior reference point on the airway tube to better conform to the anatomy, this invention provides for a wide range of flexional response that obviates the ventral displacement described by prior art.

Figure 16:
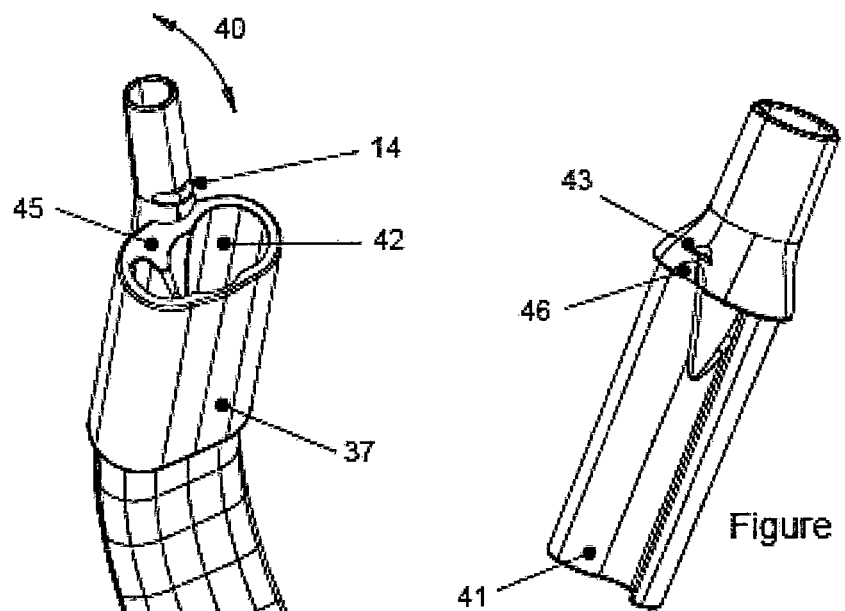
FIG. 16 is an isometric view of the body of FIG. 12.

Protruding from the external surface of the gastric drain tube opening in closest proximity to the adaptor (FIG. 16), a raised step 14 is defined that has a corresponding cut out (FIG. 17) or notch 43 in the outer surface of the adaptor. This raised step retains and prevents the adaptor from separating away from the airway tube (FIG. 20). When viewed superiorly toward the distal tip (FIG. 7), the proximal end 12 of the gastric drain tube is aligned with the median plane of the airway tube i.e. both passages share common a mid-plane (FIG. 7). It must be noted that the mid-plane of the airway tube is with reference to the lateral extremities of the airway tube rather than an alignment with the primary or secondary passage. To provide a primary passage of sufficient internal diameter to accommodate the insertion of an ETT and blind intubation, the third passage is laterally offset and divided by an impermeable barrier (posterior surface of airway tube) to ensure simultaneous blind intubation and gastric access.

Figure 2:
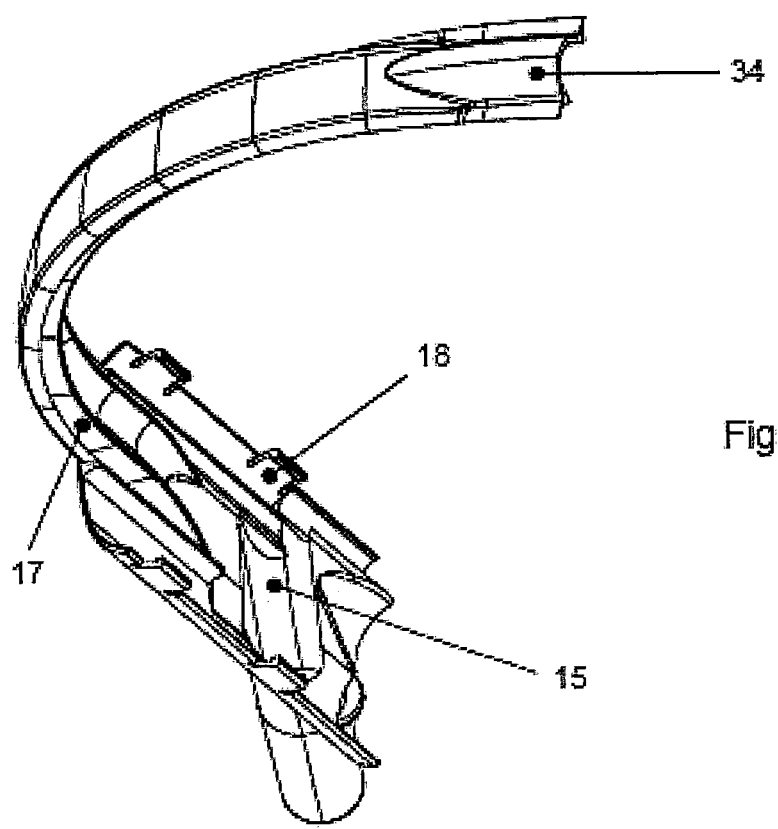
FIG. 2 is an isometric view of an insert for the body of FIG. 1.

As the median axis of the proximal opening (FIG. 9) approaches an intersection with the median axis of the adaptor and airway tube 13a, the tubular cross section transitions increasingly elliptical and no longer exhibits an enclosed perimeter, having opened up 15 to straddle the proximal airway tube (FIG. 2). When a gastric drainage suction tube is inserted through the tubular feature 12, the distal tip of the suction tube will make tangential contact 16 with posterior surface of the primary passage (FIG. 3).

Further insertion deflects the suction tube laterally, seeking alignment with the supporting structure of ribs 17 defining the posterior channel or third passage in this region. The suction tube can then be guided inferiorly to exit at the distal tip of the device 20.

Proximally, the intermediate strip is attached by 4 latches, 2 per side positioned laterally 18 where the intermediate strip straddles the airway tube. Coinciding at the tangent where the straddling straight section of the airway tube terminates and the curvature 6 begins, the intermediate strip narrows abruptly 19. The supporting structure of ribs 17 follow the curvature of the airway tube 6; opposing ribs 11a integral with the intermediate strip (FIG. 6a) provide alignment and minimal interference, sufficient to provide for aforementioned attachment. Ribs 11a and 17 progressively diminish and terminate at the proximal end of the medial slot 8.

Having described the airway tube, intermediate strip and adaptor, any or all of which may be manufactured from polyolefin material; the description now focuses on the inflatable cuff manufactured from a thermoplastic elastomer (TPE) compounded from the same base polyolefin material. This in itself provides the means of assembly for the device described herein. The self-adhering property of TPE, adhere the intermediate strip to the airway tube and create an open thin walled cuff membrane by virtue of an initial injection moulding processes; a subsequent injection moulding process entraps the open membrane and creates an airtight and inflatable cuff, integral to the form and function of the device.

Figure 11:
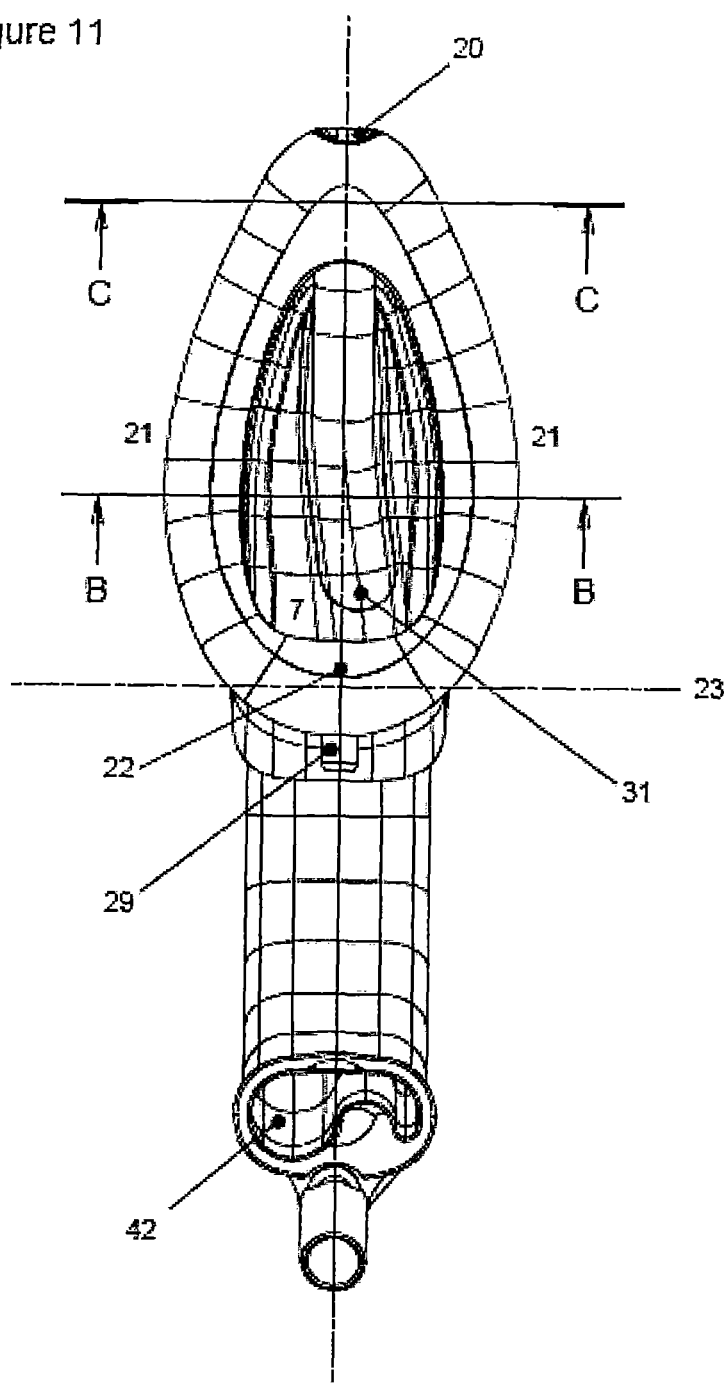
FIG. 11 is a front view of a body of an airway management device according to a further embodiment of the present invention.

Viewed anteriorly toward the frontal plane (FIG. 11), the initial injection moulding process surrounds the perimeter of the distal airway tube with an elliptical shape cuff membrane of TPE, in a generally toroidal shape about the airway tube. In a specific embodiment, the cuff membrane may be characterised by; a distal tip whose curvature and width facilitate the tubular distal opening of the third passage 20 or gastric drain tube; lateral extremities 21 defined by curvature extending superiorly and tangential to the distal tip; an increasing rate of change of curvature that closes the elliptical shape at the median plane 22, just superior to the horizontal axis through two laterally opposed slots 23 and; an enclosed third passage or gastric drain tube 24, totally covering the medial slot 9 and whose contour and curvature 31 reconcile with that of the partial posterior channel 5. It will be appreciated that in alternative embodiments, the membrane may be a variety of open shapes, which may allow closure through a second moulding process to seal the open membrane and thus permit inflation of the cuff.

Figure 12:
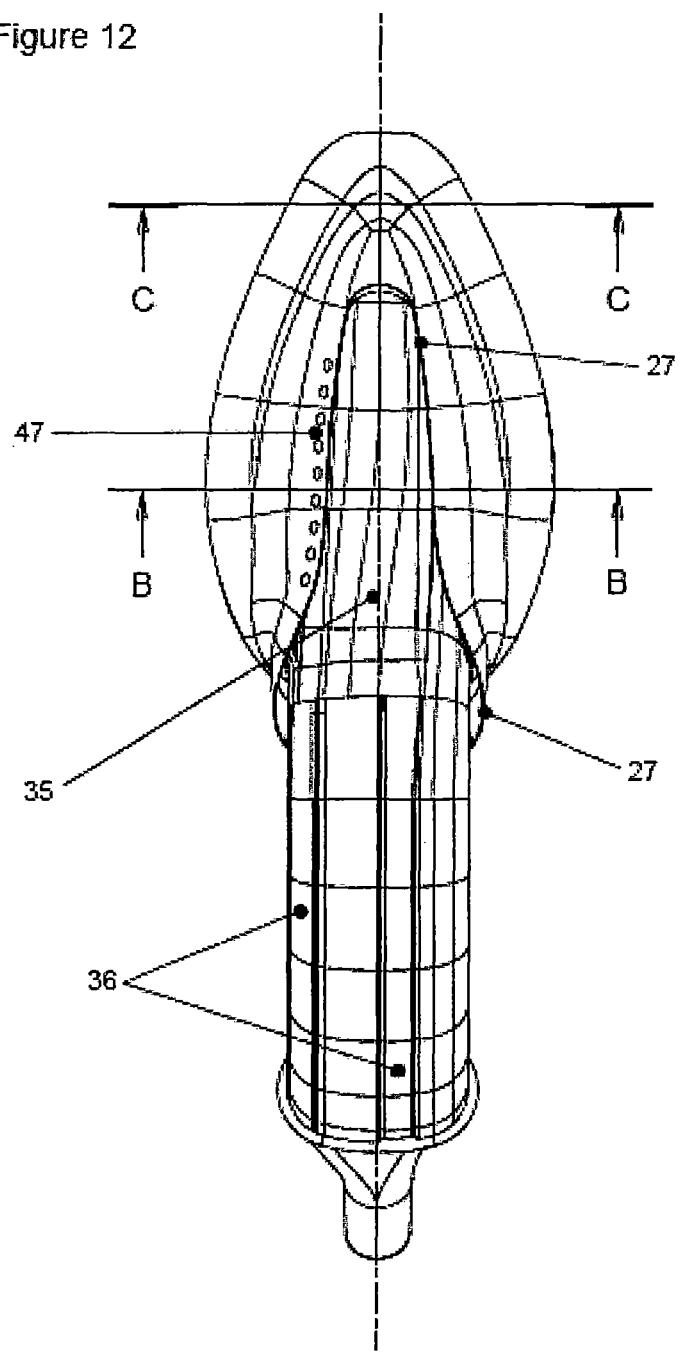
FIG. 12 is a back view of the body of FIG. 11.

Horizontal cross sections B-B and C-C (FIGS. 13 and 14) illustrate the ventral or anterior opening 7 through which the primary and secondary passages exit. With respect to FIG. 14, the perimeter of the ventral opening is defined by a thin walled inflatable cuff membrane exhibiting an elliptical section 25. Adhered in the first instance to the perimeter of distal airway tube 26 and continuing tangentially from the immediate anterior of the airway tube toward its lateral extremity and normal to the edge of the airway tube. The method of manufacturing requires the cuff membrane to be open along the posterior opening 27 of the perimeter (FIGS. 12 and 14), except for a region surrounding the distal opening (FIG. 13) of the gastric drain tube that is moulded into a closed section 28 defining the configuration of the inflatable cuff surrounding the distal drain tube. To this end, as a result of the first injection moulding step, the cuff is in the form of an open toroidal shape having the membrane open along a periphery of the toroid and adjacent to the periphery of the airway tube.

Figure 8:
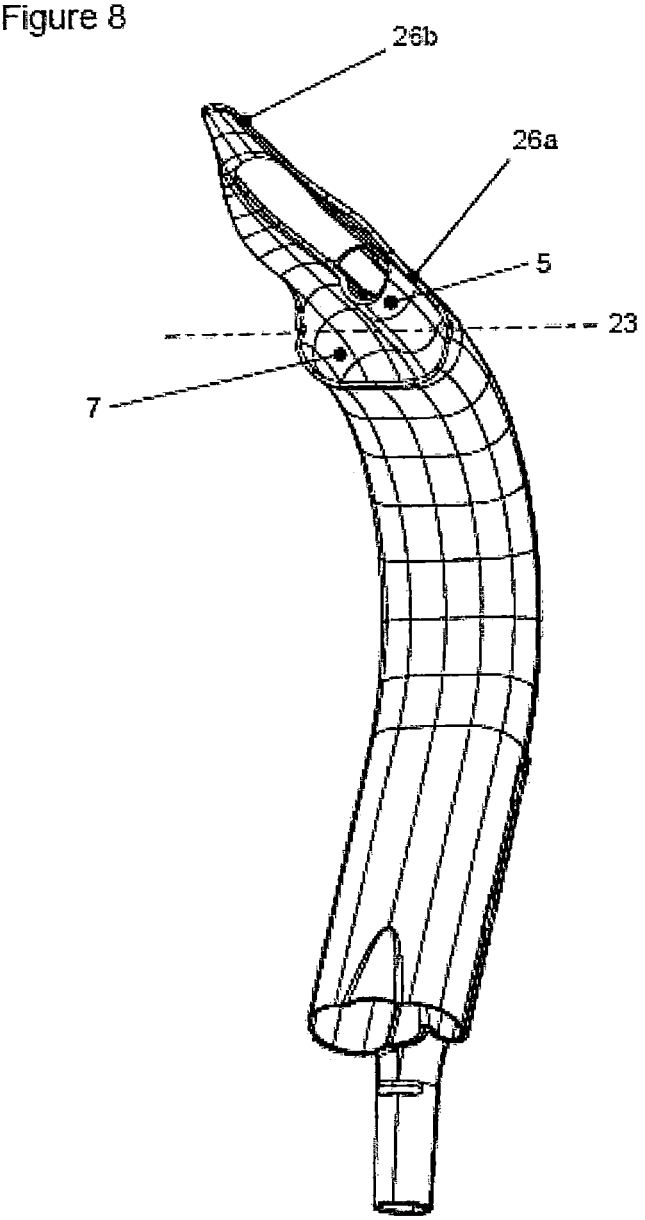
FIG. 8 is an isometric view of the body of FIG. 1.
Figure 24:
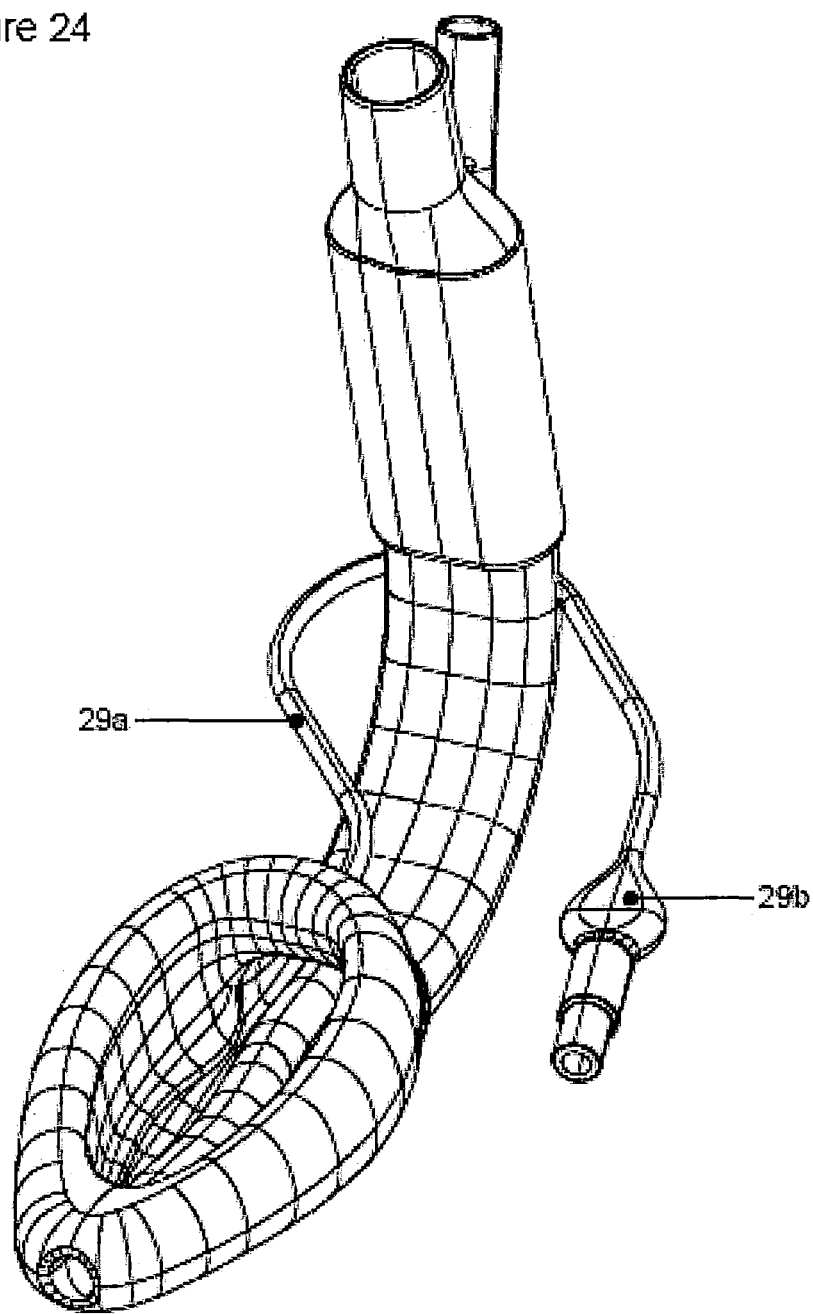
FIG. 24 is an isometric view of a body of an airway management device according to a still further embodiment of the present invention.

With reference to FIG. 8, the thickness of airway tube along the perimeter 26 varies from 1.00 26*a* to 0.5 mm 26*b* combines with the compound curvature 33 at the distal airway tube to provide flexural articulation rather than flexure of the distal tip around a fixed horizontal axis. The thickness of the inflatable cuff membrane varies between 0.25 mm (leading edge of posterior opening 27) and 1.50 mm along the perimeter of the distal airway tube 26. All other cuff membrane wall thicknesses are optimised to provide for the ideal inflated shape and mechanical strength e.g. that portion of the inflatable cuff membrane (FIGS. 11, 20 and 21) surrounding a small tubular port 29 for attaching an inflation tube 29*a* extruded from thermoplastic elastomer (FIGS. 24 and 25) and equipped at its proximal end with an inflation balloon 29*b* and check valve allowing gaseous communication with the inflatable cuff.

Figure 13:
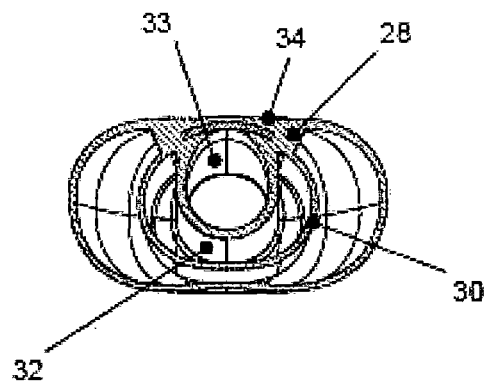
FIG. 13 is a detail cross sectional view of the body of FIG. 12.
Figure 14:
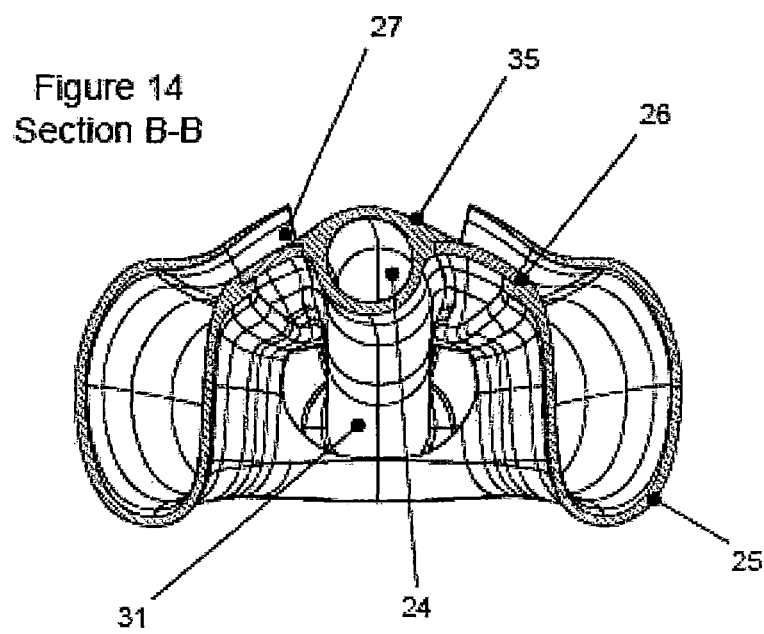
FIG. 14 is a detail cross sectional view of the body of FIG. 12.

It is a feature of this invention that the distal portion of the gastric drainage tube may not intersect the inflated volume of the cuff (FIGS. 13 and 14). In this embodiment the outside diameter may not be directly exposed to the inflation pressure within the inflatable cuff; wall thickness of the gastric drainage requires no reinforcement structure to prevent occlusion; thereby avoiding a bulbous distal cuff configuration. Instead, and consistent with the closed section 28, the inflatable cuff membrane 25 is moulded into a closed tubular section 30 concentric with the third passage or gastric drain tube 24 creating a free space, or chamber, 32 adjacent to the tip of the device, and between the inflatable membrane and the distal third passage particularly about the aperture through which the gastric drainage tube projects. When in situ and inflated, the closed section of cuff membrane 30 will not expand to an extent that all free space 32 is eliminated and the gastric drain tube 24 compressed and occluded. The chamber 32 therefore provides a an expansion buffer, the size of which may be determined through design so as to accommodate sufficient inflation of the cuff. The cuff will therefore expand to within close proximity, providing support to the third passage, or gastric drain tube 24, and the distal opening 20 against the upper oesophageal sphincter.

Furthermore, immediately superior to the distal opening, the anterior of distal airway tube compound curvature 33 defines the internal posterior surface of the third passage or gastric drain tube; the narrow width and curvature of the airway tube; the reducing thickness 26*b* and; the surrounding contour 34 of self-adhered TPE elastomer, minimise the deflated thickness of the distal tip. The elastic response of the polyolefin airway tube is manifest at the distal tip, now assisted by the softer TPE. This configuration keeps combined thickness of materials to a minimum, a characteristics evident when the cuff is deflated prior to deployment, negating the potentially bulbous nature of the distal cuff and gastric drainage supporting structure.

The contour of TPE adhering 34 to the distal anterior airway tube (FIG. 13), having defined the closed section 28, progresses superiorly along the progressive curvature 31 of the medial slot 9, blending the resultant posterior contour 35 smoothly onto the intermediate strip, where it locates against the proximal end 8 of the medial slot. At this juncture the TPE diverts either side of the intermediate strip (FIGS. 7 and 12) filling the sagittal planar voids 36 defined by the intermediate strip locating against the posterior curvature of the airway tube 6. Proximally, at the juncture of the abruptly narrowing intermediate strip 19, the TPE 37 converges to surround the latches 18 and the intermediate strip in its entirety where it straddles the airway tube; the union of the intermediate strip and the airway tube is completed. Surrounded by TPE, the sealed union creates an enclosed third passage or gastric drain tube with proximal and distal opening.

The angle 13 of the tubular feature relative to the adaptor (FIGS. 16 and 17) combined with the elastic nature of the TPE allows the user to; apply leverage to the tubular feature 12; in a direction 40 such that the angle of incidence through the retaining step 14 relative to the frontal plane (FIG. 9) is reduced and; remove the adaptor for insertion of an endotracheal tube or endoscope.

The adaptor can be returned to its original position by inserting the distal end 41 into the proximal airway tube opening 42 and pushing it posteriorly. Once the notch 43 in the adaptor encounters the raised step 14 on the tubular feature 12; a moderate increase in pressure will enable the adaptor to snap back into the home position; the mating face 44 of the adaptor (FIG. 5) is pressed into and creates an airtight seal against the TPE 45 covering the proximal end 1 airway tube and intermediate strip and; a cylindrical cut-out 46 in the adaptor provides a minimal clearance against the tubular feature 12.

The subsequent injection moulding process provides a core and cavity that locates the leading edge of the open cuff membrane 27 firmly against an airway portion such as the posterior distal airway tube perimeter 26. TPE interacts with the leading peripheral edges, entrapping them and blending with the already complete distal closed section 28 and conforming to the finished inflatable cuff contour defined by the injection mould core and cavity so as to close the toroidal cuff. A further embodiment (FIG. 12) of this interaction encourages the TPE to further entrap the leading edge via small cut-outs 47 and adhere it directly to the posterior of the distal airway tube.

Figures 18, 19:
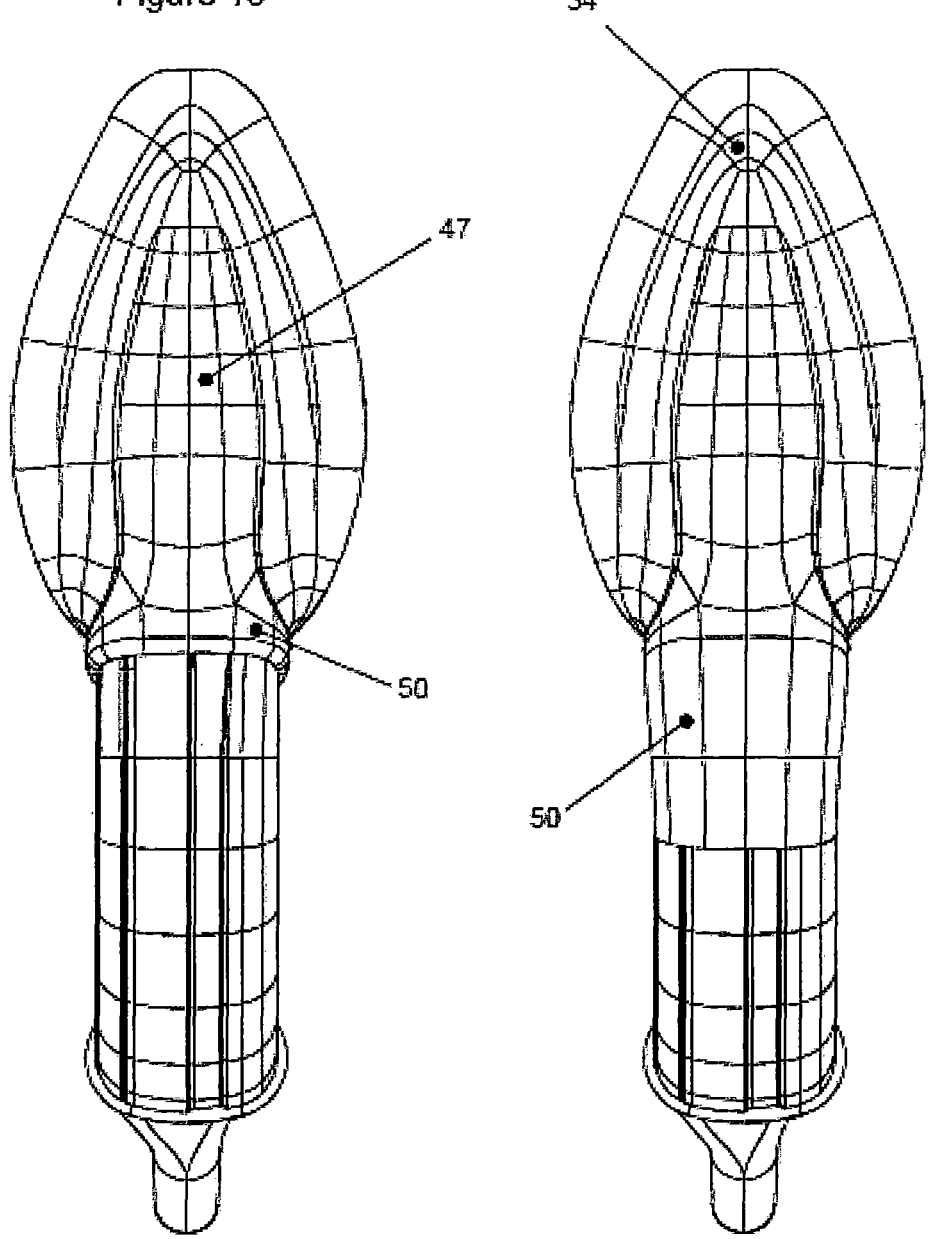
FIG. 18 is a back of a body of an airway management device according to a further embodiment of the present invention.
FIG. 19 is a back of a body of an airway management device according to a further embodiment of the present invention.

The finished contour of the distal portion (FIGS. 18, 20 and 22) adds additional TPE to the initial posterior contour 35 of the airway tube, wrapping around and completing a sealed circumference of the airway tube 48; creating an airtight inflatable cuff. A further embodiment of this circumferential blend (FIGS. 19, 21 and 23) shows the step 49 tapering away to a smooth blend 50 around the circumference of the airway tube.

The inflatable cuff membrane completes the manufacturing of the device described by this invention, without the need for adhesives or solvents. Using entirely polyolefin based materials achieves a more ecological sustainable alternative to PVC and vinyl elastomers that may contain DEHP plasticisers or, LSR that cannot be recycled and similarly re-processed due to the fact that it is a thermoset material whose cross linking during moulding cannot be reversed.

In a further aspect of the present invention, the arrangement of the passage for receiving gastric drainage tube may be applied to an airway management device of the prior art. Further, the method of manufacturing the cuff in a two part construction may also be applied as an invention separate to the shell arrangement described previously. To this end, the third passage described previously, may be a distinct and discrete addition to an airway management device and consequently may simply be described as a passage when an equivalent first and second passage, as described above is not clearly defined or in fact not present.

The invention claimed is:

1. An airway management device, comprising:
   a body having a proximal end for receiving an endotracheal tube and a distal end;

said body including a linear portion adjacent to the proximal end and a curved portion adjacent to the distal end;

said body including an external shell and having a first bore through said external shell for receiving the endotracheal tube;

wherein a cross section of the first bore includes a first passage shaped to position the endotracheal tube in one portion of the first bore for at least the linear portion of the body, so as to maintain a second passage in the remaining cross section of the first bore;

wherein the second passage is arranged to receive an endoscope, said second passage shaped to position the endoscope for at least the linear portion of the body;

wherein the body includes a third passage, said third passage arranged to receive a gastric drain tube; and wherein the body includes an intermediate strip positioned along a length of said body, said third passage defined in part by a wall of said intermediate strip.

2. The airway management device according to claim 1, wherein the intermediate strip is shaped so as to be flush with an external surface of said body.

3. The airway management device according to claim 1, further including a toroidal shaped membrane having first and second opposed edges, said first edge moulded to a first portion of the body and the second edge moulded to a second portion of the body, said first and second portions in spaced relation, the toroidal shaped membrane forming an inflatable cuff.

4. The airway management device according to claim 1, wherein the third passage extends to a tip of the distal end and terminates at an aperture arranged to permit the gastric drain tube to extend therefrom.

5. The airway management device according to claim 1, further including a receiving tube mounted to a proximal end of the third passage, said receiving tube arranged to receive the gastric drain tube.

6. The airway management device according to claim 5, wherein said receiving tube is mounted to said intermediate strip.

7. The airway management device according to claim 4, wherein the aperture is arranged such that the third passage adjacent the tip and an inflatable cuff attached to the body are discrete, so as to permit inflation of the inflatable cuff without contacting the third passage.

8. The airway management device according to claim 1, further including a chamber adjacent a tip of the body and intermediate the third passage and an inflatable cuff, said chamber providing an expansion buffer for said inflatable cuff to prevent the inflatable cuff when inflated from causing the third passage to collapse.

9. The airway management device according to claim 1, wherein the cross section of the first bore is non-symmetrical.

10. The airway management device according to claim 1, wherein the first passage is larger than the second passage.

11. An airway management device, comprising:

a body having a proximal end for receiving an endotracheal tube and a distal end;

said body including a linear portion adjacent to the proximal end and a curved portion adjacent to the distal end;

said body including an external shell and having a first bore through said external shell for receiving the endotracheal tube;

wherein a cross section of the first bore includes a first passage shaped to position the endotracheal tube in one portion of the first bore for at least the linear portion of the body, so as to maintain a second passage in the remaining cross-section of the first bore;

wherein the second passage is arranged to receive an endoscope, said second passage shaped to position the endoscope for at least the linear portion of the body;

wherein the body includes a third passage, said third passage arranged to receive a gastric drain tube;

wherein the third passage extends to a tip of the distal end and terminates at an aperture arranged to permit the gastric drain tube to extend therefrom;

wherein the aperture is arranged such that the third passage adjacent the tip and an inflatable cuff attached to the body are discrete, so as to permit inflation of the inflatable cuff without impacting the third passage.

12. The airway management device according to claim 11, further including a chamber adjacent the tip and intermediate the third passage and inflatable cuff, said chamber providing an expansion buffer for said inflatable cuff to prevent the inflatable cuff when inflated from causing the third passage to collapse.

13. The airway management device according to claim 11, further including a toroidal shaped membrane having first and second opposed edges, said first edge moulded to a first portion of the body and the second edge moulded to a second portion of the body, said first and second portions in spaced relation, the toroidal shaped membrane forming the inflatable cuff.

14. The airway management device according to claim 11, wherein the body includes an intermediate strip positioned along a length of said body, said third passage defined in part by a wall of said intermediate strip.

15. The airway management device according to claim 14, further including a receiving tube mounted to a proximal end of the third passage, said receiving tube arranged to receive the gastric drain tube.

16. The airway management device according to claim 15, wherein said receiving tube is mounted to said intermediate strip.

17. The airway management device according to claim 11, wherein the cross section of the first bore is non-symmetrical.

18. The airway management device according to claim 11, wherein the first passage is larger than the second passage.

19. An airway management device, comprising:

a body having a proximal end for receiving an endotracheal tube and a distal end;

said body including a linear portion adjacent to the proximal end and a curved portion adjacent to the distal end;

said body including an external shell and having a first bore through said external shell for receiving the endotracheal tube;

wherein a cross section of the first bore includes a first passage shaped to position the endotracheal tube in one portion of the first bore for at least the linear portion of the body, so as to maintain a second passage in the remaining cross-section of the first bore;

wherein the second passage is arranged to receive an endoscope, said second passage shaped to position the endoscope for at least the linear portion of the body;

wherein the body includes a third passage, said third passage arranged to receive a gastric drain tube;

further including a receiving tube mounted to a proximal end of the third passage, said receiving tube arranged to receive the gastric drain tube and mounted to an intermediate strip forming part of said body.

20. The airway management device of claim 19, wherein the third passage extends to a tip of the distal end and terminates at an aperture arranged to permit the gastric drain tube to extend therefrom.

21. The airway management device of claim 20, wherein the aperture is arranged such that the third passage adjacent the tip and an inflatable cuff attached to the body are discrete.

22. The airway management device of claim 20, further including a chamber adjacent the tip and intermediate the third passage and an inflatable cuff, said chamber providing an expansion buffer for said inflatable cuff to prevent the inflatable cuff when inflated from causing the third passage to collapse.

23. The airway management device according to claim 19, further including a toroidal shaped membrane having first and second opposed edges, said first edge moulded to a first portion of the body and the second edge moulded to a second portion of the body, said first and second portions in spaced relation, the toroidal shaped membrane forming an inflatable cuff.

24. The airway management device according to claim 19, wherein the intermediate strip is positioned along a length of said body, said third passage defined in part by a wall of said intermediate strip.

25. The airway management device according to claim 19, wherein the cross section of the first bore is non-symmetrical.

26. The airway management device according to claim 19, wherein the first passage is larger than the second passage.

* * * * *